United States Patent [19]

Sohngen

[11] Patent Number: 5,047,034
[45] Date of Patent: Sep. 10, 1991

[54] INTRAMEDULLARY ROD SCREW GUIDE

[75] Inventor: Gary W. Sohngen, Los Angeles, Calif.

[73] Assignee: ACE Orthopedic Manufacturing, Los Angeles, Calif.

[21] Appl. No.: 529,529

[22] Filed: May 29, 1990

[51] Int. Cl.⁵ ............................................. A61F 5/04
[52] U.S. Cl. ....................................... 606/87; 606/96
[58] Field of Search ...................... 606/79, 87, 89, 90, 606/96, 98, 53, 54, 80, 86, 87; 623/16

[56] References Cited

U.S. PATENT DOCUMENTS

| | | | |
|---|---|---|---|
| 4,103,683 | 8/1978 | Neufeld | 606/96 |
| 4,622,959 | 11/1986 | Marcus | 606/64 |
| 4,911,153 | 3/1990 | Border | 606/98 |

Primary Examiner—David J. Isabella
Assistant Examiner—R. Clarke
Attorney, Agent, or Firm—Grant L. Hubbard

[57] ABSTRACT

An intramedullary rod screw guide for use in orthopedic surgical procedures involving the installation of an intramedullary rod comprising means for attaching the guide to an external support assembly during installation of an intramedullary rod, a laterally extending spacer plate, intramedullary rod attachment means proximate the distal end of the spacer plate and guide means secured to the spacer plate intermediate the proximal and distal ends thereof, the guide means forming a passage which, in use, is aligned with the bone screw passage in the intramedullary rod permitting the guided insertion of drill means and bone screw insertion means through the guide passage in alignment with the bone screw passage in the intramedullary rod.

2 Claims, 2 Drawing Sheets

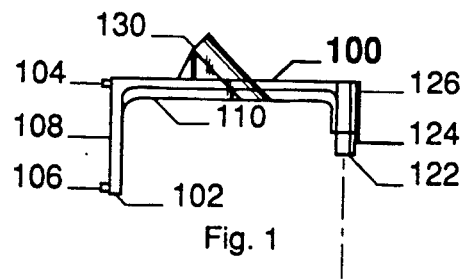
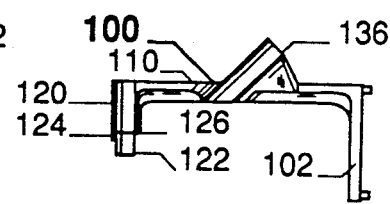
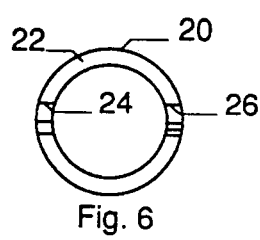
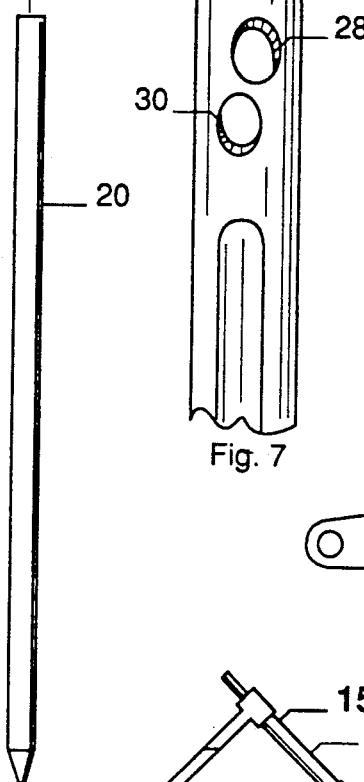
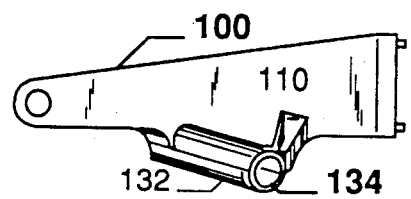
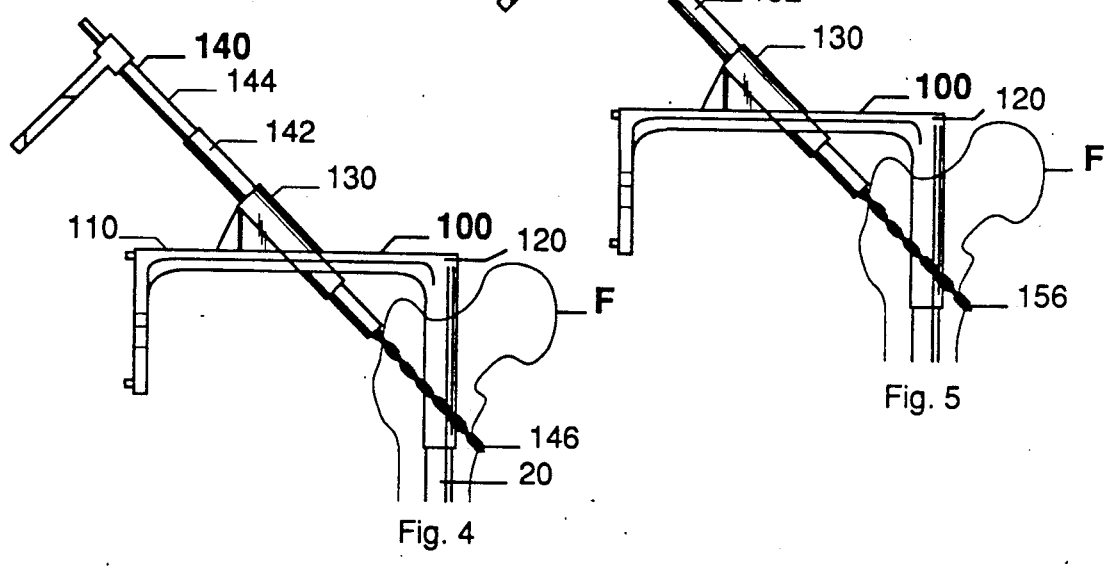

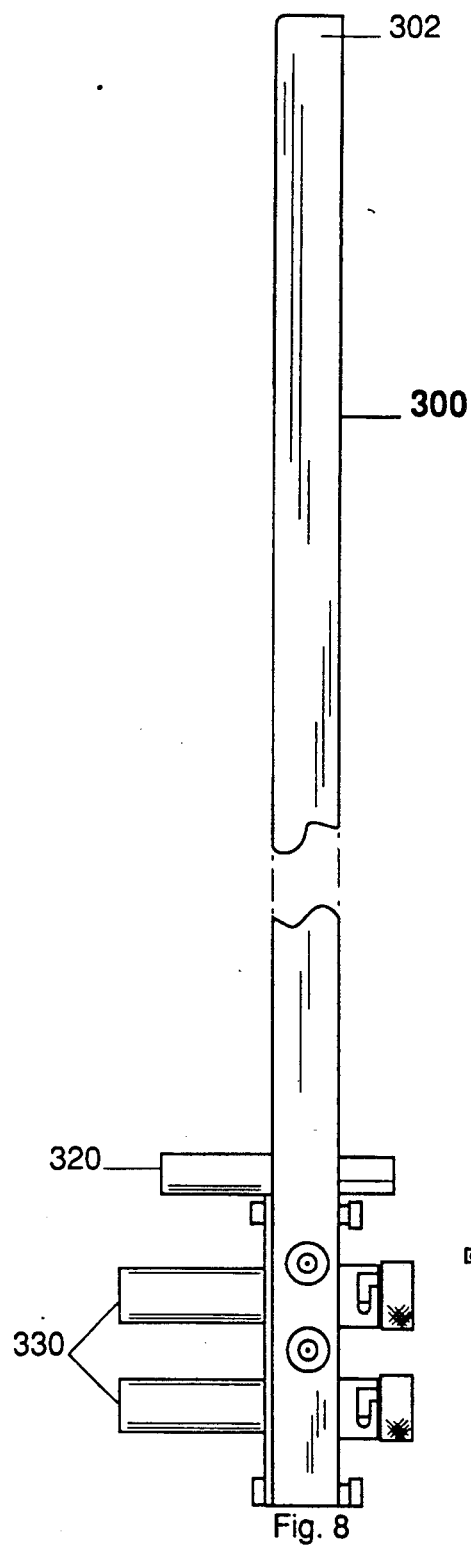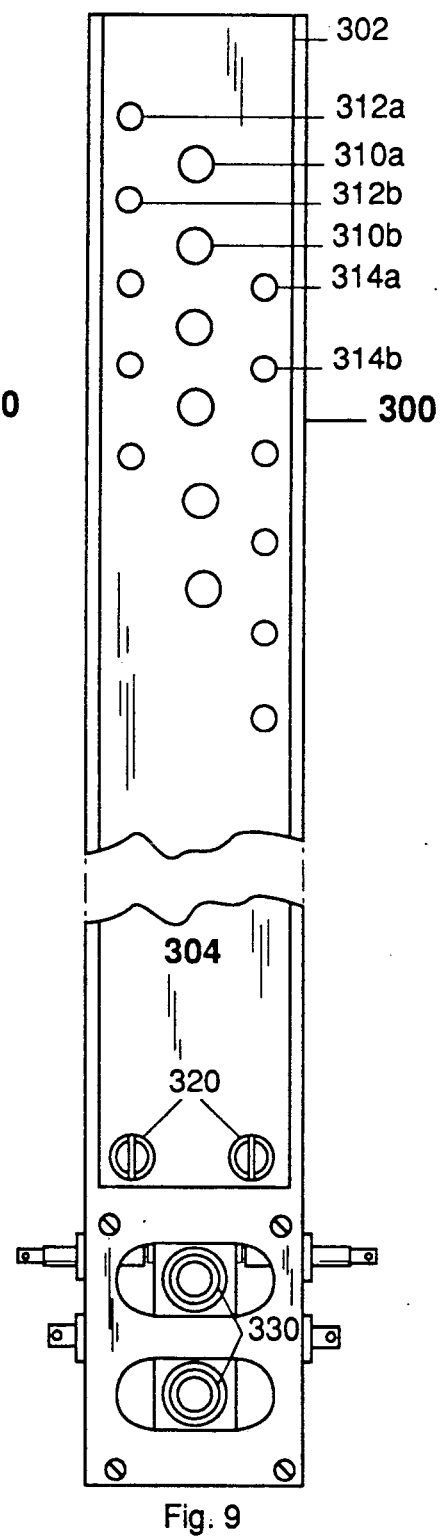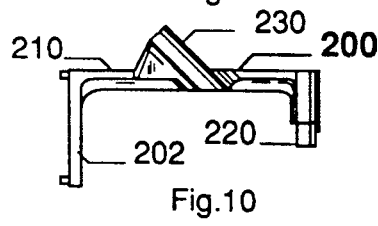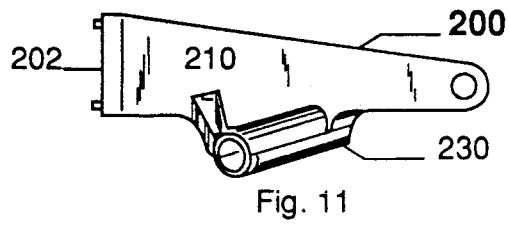

INTRAMEDULLARY ROD SCREW GUIDE

FIELD OF THE INVENTION

This invention relates to surgical devices and, more particularly, to devices for positioning intramedullary rods in the femur of a patient and for targeting the screws for passage through apertures in the intramedullary rod for affixing the rod in the femur.

BACKGROUND OF THE INVENTION

Intramedullary rods are widely used in orthopedic surgery to fix certain broken bones and to maintain the bone fragments in the proper alignment during healing and to provide strength during the convalescence of the patient.

One such intramedullary rod with which the present invention is most useful is described by Zindrick and Sohngen in patent application Ser. No. 230,563, filed Aug. 10, 1988. This intramedullary rod is referred to generally herein, but reference is made to said patent application for a more complete and detailed description.

It is necessary, in most instances, to affix the intramedullary rod to one or both fragments of the bone using bone screws or other fasteners. Thus, intramedullary rods are provided with a plurality of apertures therethrough for receiving screws or fasteners of various configurations. Fixation of the intramedullary rod requires that these apertures be precisely located, that passages be drilled through the compact cortical tissue and the cancellous tissue of the bone and that the fastener screws be secured in the bone tissue through the apertures in the intramedullary rod to fix the intramedullary rod in the proper relationship with the bone fragments.

X-ray viewers or x-ray films are widely used to display the relationship of the bone fragments, intramedullary rod and, after installation, the fastener screws. Many such viewing devices and systems are available. The present invention is useful with targeting devices which are specifically designed to guide the installation of distal bone screws through apertures in the intramedullary rod, but may be used with any intramedullary rod installation device which includes an external support assembly which carries or is adapted to support and position such targeting devices.

The present invention is specifically designed and most advantageously used in connection with the targeting device described in U.S. Pat. No. 4,881,535, Nov. 21, 1989, to Sohngen, but may be used with other external support assembly type devices for installing intramedullary rods.

SUMMARY OF THE INVENTION

The present invention is an improved intramedullary rod screw guide for use in orthopedic surgical procedures involving the installation of an intramedullary rod. The guide comprises four basic structures.

An attachment plate portion comprises means for affixing the jig to an external support assembly. The attachment plate portion is generally planar and, in use, extends generally parallel to, and spaced from, the intramedullary rod being installed, and during installation of the intramedullary rod is attached to the external support assembly which is used to guide the drilling of bone screw holes in alignment with passages in the proximal end of the intramedullary rod.

A laterally extending spacer plate portion having a proximal end and a distal end is secured at its proximal end to the attachment plate portion and extends generally perpendicular thereto. Intramedullary rod attachment means are provided proximate the distal end of the spacer plate, and guide means are secured to the spacer plate intermediate the proximal and distal ends thereof.

The guide means comprises a guide boss secured to the spacer plate having formed therethrough a cylindrical guide passage having a central axis extending at a non-perpendicular angle relative to the spacer plate for receiving bone drill means and bone screw insertion means.

The attachment plate portion, spacer plate portion, intramedullary rod attachment portion and the guide means are constructed and configured so as to permit the attachment plate portion to be secured to an external support assembly and the intramedullary rod attachment means to be secured to an intramedullary rod which has at least one bone screw passage therethrough to be secured thereto during installation of the intramedullary rod. The central axis of the guide passage in the guide boss is aligned with the bone screw passage in the intramedullary rod permitting the guided insertion of drill means and bone screw insertion means through the guide passage in alignment with the bone screw passage in the intramedullary rod.

An intramedullary rod screw guide is depicted and generally described in U.S. Pat. No. 4,622,959, Nov. 18, 1986, to Marcus. The Marcus device is constructed to be secured to and supported by an already installed intramedullary rod and is not suitable for use with an external support assembly which constitutes, supports or mounts a targeting device for installation of the proximal bone screws. Thus, the Marcus device is in the nature of an auxiliary or supplemental device and not part of an overall intramedullary rod installation system. The present invention is multi-functional and an integral part of an intramedullary rod installation system.

BRIEF DESCRIPTION OF THE DRAWINGS

FIG. 1 is an exploded elevational view of the intramedullary rod screw guide of this invention and of an intramedullary rod which would be connected thereto in use.

FIG. 2 is an elevational view of the intramedullary rod screw guide of this invention taken from the other side, with respect to the view in FIG. 1.

FIG. 3 is a top plan view of the intramedullary rod screw guide of this invention.

FIG. 4 depicts the intramedullary rod screw guide of this invention in use guiding a drill through a bone screw aperture in an intramedullary rod.

FIG. 5 depicts the intramedullary rod screw guide of this invention in use guiding and positioning a bone screw through an aperture in an intramedullary rod, as would be shown in use.

FIG. 6 is a top view of an intramedullary rod of a type which may be used with this invention, showing the distal end thereof.

FIG. 7 is a plan view showing the side of the upper or distal portion of an intramedullary rod of the type which may be used with this invention, showing the bone screw passages therethrough.

FIG. 8 depicts the external support assembly, shown in side elevational view, of the type which is used for targeting the proximal bone screws through an intramedullary rod, with which the present invention may be used and combined as a system.

FIG. 9 is a plan view of the external support assembly of FIG. 8.

FIG. 10 is a side elevational view of a right-handed version of the intramedullary rod screw guide of this invention.

FIG. 11 is a top plan view of the intramedullary rod screw guide of FIG. 10, showing the right-handed version.

DESCRIPTION OF THE PREFERRED EMBODIMENT

In one embodiment the present invention comprises a system for installing intramedullary rods, the particular example used in the drawings and in the following description being the installation of a femur intramedullary rod. The system comprises an external support assembly 300 which is described in complete detail as in U.S. Pat. No. 4,881,535, with which the intramedullary rod screw guide 100, in the left-hand version, or 200, in the right-hand version, is combined for the installation of an intramedullary rod such as that shown at 20 in FIG. 1. The external support assembly 300 comprises an external channel support member 302 formed of rigid metal, preferably titanium, which comprises a web portion 304 and flange portions 306 and 308. The web portion has formed therein a plurality of connector screw apertures 310 spaced generally along the center of the web and one or two series of alignment pin apertures 312 and 314. These apertures permit the instrument of the intramedullary rod screw guide of this invention to the external support assembly and the very precise positioning of the screw guide on the external support assembly. In the particular embodiment shown in FIGS. 8 and 9 and described in detail in U.S. Pat. No. 4,881,535, a plurality of x-ray alignment tubes 320 and guide sleeves 330 are provided for targeting the bone screws in alignment with the bone screw passages in the proximal, or lower, end of the intramedullary rod.

For convenient reference, the term "proximal" is used with respect to the intramedullary rod to indicate the rounded end of the intramedullary rod which is first inserted into the femur and the "distal" end of the intramedullary rod is used to refer to that end of the intramedullary rod which is connected to the rod screw guide and which is the last portion of the rod to enter the femur.

Referring now with particularity to FIGS. 1, 2 and 3, the intramedullary rod screw guide of this invention comprises an attachment plate portion 102 which has, in the preferred embodiment, one or more alignment bosses or pins 104 and 108 extending therefrom for being received in the alignment apertures 310 and 312 in the external support assembly for fixing the location of the intramedullary rod screw guide on the external support assembly. An aperture 108 through the attachment plate portion may receive a screw or bolt for providing firm securement of the attachment plate portion to the external support assembly. In use, as depicted in FIG. 1, the attachment plate portion extends generally parallel to, and spaced from, the intramedullary rod which is being installed. In the preferred embodiment, the attachment plate portion is generally planar for being secured in a precisely aligned location on the external support assembly.

A laterally extending spacer plate portion 110 is connected at the proximal end thereof to the attachment plate portion and extends generally perpendicular thereto. Intramedullary rod attachment means 120 is affixed or secured proximate the distal end of the spacer plate 110. The attachment means may comprise an insertion pin 122, an orientation boss 124, and an intramedullary rod abutting boss 126. The intramedullary rod orientation boss 124 is configured to be received in the notch 24 or the notch 26 of the intramedullary rod 20, as best shown in FIG. 6, which shows the distal end 22 of the rod. Referring briefly to FIG. 7, proximate the distal end of the intramedullary rod are one or more, usually two, bone screw passages 28 and 30 extending through the rod. Such passages are often intersecting passages, and only one is used in any given circumstance. A great variety of intramedullary rods may, however, be used with the present invention.

Intermediate the proximal and distal ends of the spacer plate, guide means, generally indicated at 130, are formed or secured. The guide means, in the preferred embodiment, comprises a boss 132 formed integral with or secured, for example by a weldment, to the spacer plate 110. The guide boss has formed therethrough a cylindrical passage 134 which, being cylindrical, inherently has a central axis, not shown. The central axis extends at a non-perpendicular angle relative to the spacer plate. The passage is constructed and adapted to receive bone drill means and bone screw insertion means, as will be described. A web 136 may be formed or added for strength and stability in securing the boss to the spacer plate.

Referring now to FIG. 4, a bone drill assembly 140, comprising a guide sleeve 142 which is held snugly and firmly in the cylindrical guide passage 134, permits rotation of a drill actuator 144 for rotating the drill 146 for drilling a hole through the bone, the drill being so aligned as to extend through the bone screw apertures in the intramedullary rod 20.

In a similar manner, the cylindrical guide passage in the guide boss snugly receives a guide tube 152 which guides and holds a screw driver mechanism 154 for screwing a bone screw 156 into the bone and through an aperture in the intramedullary rod.

The guide boss is secured to the spacer plate and has formed therethrough the cylindrical passage having a central axis extending at a non-perpendicular angle relative to the spacer plate for receiving the bone drill means and, at a different time, the bone screw insertion means. The attachment plate portion, the spacer plate portion, the intramedullary rod attachment portion and the guide means are constructed and configured such that the attachment plate portion can be secured to the external support assembly and the intramedullary rod attachment means secured to the intramedullary rod, which has at least one bone screw passage therethrough, to be secured during the installation of the intramedullary rod. The central axis of the guide passage and the guide boss is aligned with the bone screw passage in the intramedullary rod, thus permitting the drill and the screw to pass therethrough. The combination of the external support assembly 300, depicted in FIGS. 8 and 9, with the intramedullary rod screw guide depicted in FIGS. 1, 2 and 3, comprises intramedullary rod installation assembly which permits the insertion of the intramedullary rod into the bone to be repaired, and guides the installation of bone screws at both the proximal and the distal ends of the intramedullary rod, all as an integrated system. This integration of the entire system is made possible by the securement of the intramedullary rod screw guide to the external support assembly, in combination with the guide means for guiding a drill or screw into the bone screw-receiving aperture proximate the distal end of the intramedullary rod.

In the preceding figures, a left-handed intramedullary rod screw guide is depicted. The screw guide is referred to as being left-handed by reference to the attachment plate portion, i.e. looking from the attachment plate portion, as shown best in FIG. 3, the guide boss and guide means on the left-hand side of the spacer plate, and the axis of the cylinder extends from the left hand downwardly and toward the right hand of the viewer.

FIGS. 10 and 11 depict the mirror image of the intramedullary rod screw guide previously described, being a right-handed version thereof, but otherwise being identical. In the right-handed version of the intramedullary rod screw guide 200, the attachment plate portion 202 corresponds to the attachment plate portion 102 previously described, the laterally extending spacer plate portion 210 corresponds to the laterally extending plate portion 110 previously described, the intramedullary rod attachment means 220 corresponds to the previously described attachment means 120, and the guide means 230 corresponds to the previously described guide means 130.

Using the right-handed and left-handed broad screw guides, respectively, the bone screw can be inserted from either the left or the right through the intramedullary rod.

INDUSTRIAL APPLICATION

This invention is useful in orthopedic surgery.

What is claimed is:

1. An intramedullary rod installation assembly for use in the installation of an intramedullary rod, comprising:

an intramedullary rod having a proximal end and a distal end, a plurality of bone screw passages therethrough proximate the proximal end and a plurality of bone screw passages therethrough proximate the distal end thereof;

an external support assembly comprising locator means for guiding the installation of a bone screw through an aperture in an intramedullary rod proximate the proximal end thereof, the locator means comprising an external channel support member formed of rigid metal, the channel support member comprising a web portion and flange portions, the web portion having formed therein a plurality of connector screw apertures spaced generally along the center of the web and x-ray alignment means for targeting the bone screws in alignment with the bone screw passages in the proximal end of the intramedullary rod; and an intramedullary rod screw guide comprising;

an attachment plate portion comprising means for affixing the intramedullary rod screw guide to an external support assembly, said attachment plate portion being generally planar and, in use, extending generally parallel to and spaced from the intramedullary rod being installed;

a laterally extending spacer plate portion having a proximal end and a distal end, the proximal end being secured to the attachment plate portion and extending generally perpendicular thereto;

intramedullary rod attachment means proximate the distal end of the spacer plate; and guide means secured to the spacer plate intermediate the proximal and distal ends thereof, said guide means comprising;

a guide boss secured to the spacer plate having formed therethrough a cylindrical guide passage having a central axis extending at a non-perpendicular angle relative to the spacer plate for receiving bone drill means and bone screw insertion means;

connecter screws extending through the connector screw apertures securing the attachment plate portion to the external support assembly; and means securing the intramedullary rod attachment means to the distal end of the intramedullary rod;

the intramedullary rod screw guide, intramedullary rod, and locator means being constructed and configured so as to permit the guided insertion of drill means and bone screw insertion means through the guide passage in alignment with the bone screw passage in the intramedullary rod.

2. The intramedullary rod screw guide of claim 1 wherein the attachment plate portion, laterally extending spacer plate portion, intramedullary rod attachment means and the guide means are secured together as one unitary body.

* * * * *